US008000798B2

(12) United States Patent
Gantz et al.

(10) Patent No.: US 8,000,798 B2
(45) Date of Patent: Aug. 16, 2011

(54) COCHLEAR IMPLANT SYSTEM SUBSTANTIALLY PRESERVING THE HYDRODYNAMIC NATURE OF THE COCHLEA

(75) Inventors: Bruce J Gantz, Iowa City, IA (US); James Finlay Patrick, Roseville (AU); John L Parker, Roseville (AU)

(73) Assignees: Cochlear Limited, Macquarie University, NSW; University of Iowa Research Foundation, Iowa City, IA (US)

( * ) Notice: Subject to any disclaimer, the term of this patent is extended or adjusted under 35 U.S.C. 154(b) by 522 days.

(21) Appl. No.: 11/711,116

(22) Filed: Feb. 27, 2007

(65) Prior Publication Data

US 2007/0203557 A1 Aug. 30, 2007

Related U.S. Application Data

(62) Division of application No. 10/518,811, filed as application No. PCT/AU03/00828 on Jun. 27, 2003.

(30) Foreign Application Priority Data

Jun. 28, 2002 (AU) .......................... PS3227

(51) Int. Cl.
*A61N 1/39* (2006.01)
(52) U.S. Cl. ........................................................ 607/57
(58) Field of Classification Search .............. 607/55–57, 607/136, 137; 623/10; 600/379
See application file for complete search history.

(56) References Cited

U.S. PATENT DOCUMENTS

| 3,819,875 | A | | 6/1974 | Velmans |
| 4,261,372 | A | | 4/1981 | Hansen et al. |
| 4,487,210 | A | | 12/1984 | Knudsen et al. |
| 4,532,930 | A | | 8/1985 | Crosby et al. |
| 5,143,090 | A | | 9/1992 | Dutcher et al. |
| 5,594,174 | A | | 1/1997 | Keefe |
| 5,626,629 | A | * | 5/1997 | Faltys et al. ................... 607/57 |

(Continued)

FOREIGN PATENT DOCUMENTS

AU 2005201999 11/2005

(Continued)

OTHER PUBLICATIONS

Gantz, et al. "Combining Acoustic and Electrical Hearing" Laryngoscope, 113 (Oct. 2003), p. 1726-1730.

(Continued)

*Primary Examiner* — Mark W Bockelman
(74) *Attorney, Agent, or Firm* — Kilpatrick Townsend & Stockton LLP (57) ABSTRACT

An electrode array (30) which is able to be inserted to a desired depth within the cochlea to provide useful percepts for the recipient which will also preferably not cause damage to the sensitive structures of the cochlea. The electrode array (30) is insertable through an opening in the cochlea and into at least the basal region of the cochlea and comprises an elongate carrier (31) having a proximal end, a distal end, and a plurality of electrodes (32) supported by the carrier at respective spaced locations thereon in a region between the proximal end and the distal end. A stabilising collar (35) extends outwardly from the elongate carrier (31) at or adjacent a proximal end thereof and has an abutment surface adapted to abut a portion of the cochlea surface around the cochleostomy and at least substantially prevent movement of the carrier (31) following completion of insertion of the array (30) into the cochlea.

13 Claims, 6 Drawing Sheets

U.S. PATENT DOCUMENTS

| | | | |
|---|---|---|---|
| 5,758,651 | A | 6/1998 | Nygard et al. |
| 5,776,179 | A | 7/1998 | Ren et al. |
| 5,792,072 | A | 8/1998 | Keefe |
| 5,922,017 | A | 7/1999 | Bredberg et al. |
| 5,991,663 | A | 11/1999 | Irlicht et al. |
| 6,070,105 | A * | 5/2000 | Kuzma ......................... 607/137 |
| 6,119,044 | A | 9/2000 | Kuzma |
| 6,157,861 | A | 12/2000 | Faltys et al. |
| 6,163,729 | A | 12/2000 | Kuzma |
| 6,231,604 | B1 | 5/2001 | von Ilberg |
| 6,259,951 | B1 | 7/2001 | Kuzma et al. |
| 6,308,101 | B1 | 10/2001 | Faltys et al. |
| 6,415,185 | B1 | 7/2002 | Maltan |
| 6,487,453 | B1 | 11/2002 | Kuzma et al. |
| 6,498,954 | B1 | 12/2002 | Kuzma et al. |
| 6,556,870 | B2 | 4/2003 | Zierhofer et al. |
| 6,628,991 | B2 | 9/2003 | Kuzma et al. |
| 6,754,537 | B1 | 6/2004 | Harrison et al. |
| 6,889,094 | B1 | 5/2005 | Kuzma et al. |
| 6,915,166 | B1 | 7/2005 | Stecker et al. |
| 2004/0133250 | A1 | 7/2004 | Ball et al. |
| 2004/0225336 | A1 | 11/2004 | Milojevic et al. |
| 2005/0101878 | A1 | 5/2005 | Daly et al. |
| 2005/0245991 | A1 | 11/2005 | Faltys et al. |
| 2005/0256561 | A1 | 11/2005 | Gantz et al. |
| 2005/0261748 | A1 | 11/2005 | van Dijk |
| 2006/0287690 | A1 | 12/2006 | Bouchataoui et al. |
| 2007/0179566 | A1 | 8/2007 | Gantz et al. |

FOREIGN PATENT DOCUMENTS

| | | |
|---|---|---|
| AU | 2005203696 | 11/2005 |
| WO | WO 96/31087 | 10/1996 |
| WO | WO 97/26943 | 7/1997 |
| WO | WO 00/69513 | 11/2000 |
| WO | WO 00/71063 | 11/2000 |
| WO | 02/082982 | 10/2002 |
| WO | 2004/004413 | 1/2004 |

OTHER PUBLICATIONS

International Search Report for PCT/AU03/00828 dated Sep. 2, 2003.

International Preliminary Examination Report for PCT/AU03/00828 dated Oct. 8, 2004.

Written Opinion for PCT/AU03/00828 dated Oct. 16, 2003.

* cited by examiner

COCHLEAR IMPLANT SYSTEM SUBSTANTIALLY PRESERVING THE HYDRODYNAMIC NATURE OF THE COCHLEA

CROSS-REFERENCE TO RELATED APPLICATIONS

This application is a divisional application of U.S. patent application Ser. No. 10/518,811 entitled "Cochlear Implant Electrode Array" and filed on Dec. 22, 2004. The entire disclosure and contents of the above application is hereby incorporated by reference.

STATEMENT REGARDING FEDERALLY SPONSORED RESEARCH OR DEVELOPMENT

This invention was made partially with government support under Grant No. DC000242-19 awarded by the National Institutes of Health. The government has certain rights in the invention.

FIELD OF THE INVENTION

The present invention relates to an implantable cochlear electrode assembly. A method of implanting such a device is also described.

BACKGROUND OF THE INVENTION

In modern society, the occurrence of hearing loss is quite common, with approximately 10% of the population suffering from some degree of hearing impairment. This can be attributed to a number of causes, such as prolonged exposure to loud sounds, the result of disease or illness, or congenital problems.

Hearing loss is generally of two types, namely conductive and sensorineural. Conductive hearing loss occurs when the normal mechanical pathways for sound to reach the hair cells in the cochlea are impeded, for example, by damage to the ossicles. In such cases, the hearing loss may often be improved by the use of conventional hearing aids, which amplify the sound so that acoustic information reaches the cochlea and the hair cells. Such hearing aids utilise acoustic mechanical stimulation, whereby the sound is amplified according to a number of varying techniques, and delivered to the inner ear as mechanical energy. This may be through a column of air to the eardrum, or direct delivery to the ossicles of the middle ear.

Sensorineural hearing loss, however, is due to the absence or destruction of the hair cells in the cochlea which are needed to transduce acoustic signals into auditory nerve impulses. Individuals suffering from this type of hearing loss are unable to derive any benefit from conventional hearing aid systems, no matter how loud the acoustic stimulus is made, because their mechanisms for transducing sound energy into auditory nerve impulses have been damaged. In such cases, cochlear implants have been developed to provide the sensation of hearing to such individuals. In cochlear implants, electrical stimulation is provided via stimulating electrodes positioned as close as possible to the nerve endings of the auditory nerve, essentially bypassing the role of the hair cells in a normally functioning cochlea. The application of a stimulation pattern to the nerve endings causes impulses to be sent to the brain via the auditory nerve, resulting in the brain perceiving the impulses as sound.

As has been alluded to above, the treatment of both of these types of hearing loss has been quite different, relying on two quite different principles to deliver sound signals to be perceived by the brain as sound. It has been found that it is relatively common in hearing impaired individuals to experience sensorineural hearing loss for sounds in the high frequency range, and yet still be able to discern sounds in the middle to low frequency range, through the use of a conventional hearing aid, or naturally. Traditionally, in the majority of such cases, the individual would only receive treatment to preserve and improve the hearing for the middle to low frequency sounds, most probably via a conventional hearing aid, and little would be done to attempt to restore the hearing loss for the high frequency sounds. Only if the individual lost the ability to perceive the middle to low frequency sounds would consideration then be given to restoring the hearing loss for the high frequency sounds, in this case a cochlear implant would be considered a possible solution.

The specification for U.S. Pat. No. 6,231,604 introduces the concept of combining the two treatments, namely acoustic mechanical stimulation and electrical stimulation, for individuals with some degree of intact residual hearing. In this patent, the preferred embodiment makes mention of acoustic mechanical stimulation being used for sounds representative of low to mid-range frequencies in the acoustic environment, with electrical stimulation being used for sounds representative of mid to high-range frequencies in the acoustic environment. Whilst this patent identifies the need to attempt to combine the two stimulation methods it fails to suggest how such a system can be achieved, and the mechanism for performing this task.

International patent publication WO 00/69513 describes a number of embodiments of an electrode array that may be used to deliver electrical stimulation to the associated regions of the cochlear in order to supplement hearing of high frequency sounds. In this publication, a relatively short and thin electrode array is described as being between 6-8 mm in length and which is inserted through a small slit in the round window membrane for stimulation of the basal end of the scala tympani duct of the cochlea. In order to maintain the hydrodynamic nature of the cochlea, the described electrode array is provided with flexible flaps at its proximal end to assist in sealing the round window membrane and also to maintain the array in a position that is remote from both walls of the cochlea.

Experimental tests have shown that electrode arrays inserted to a depth as described by the above international patent publication will produce unnatural and sharp or high-pitched percepts in a recipient. Trials of such an array to a depth of 8 mm into the cochlea have indicated that recipients are not able to fuse the electrical stimulus with the auditory stimulus received. Therefore, the electrode array as described by the above-referenced patent publication will be unable to provide benefit to the recipient because of restriction in depth of insertion which is mandatory to preserve residual hearing. Further, the electrode array of the above-referenced patent publication will most likely cause damage to the basal membrane due to rotation or twisting of the array about its longitudinal axis. As the array relies upon flexible flaps for stabilisation and not the fixation of the head of the device, it is highly likely, due to the rounded shoulder of the device, that the array will not be stable within the cochlea, potentially causing damage to the sensitive structures therein. In addition, placement of such a device through the round window membrane may interfere with the micromechanics of the travelling wave of the inner ear.

The present invention is an attempt to address the perceived problems of such prior art devices.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention aims to ameliorate the problems associated with the prior art and provide an electrical stimulation device which is able to restore high frequency sound perception whilst allowing natural hearing mechanisms to be restored and maintained for perception of low to medium frequency sounds.

The present invention also preferably aims to provide a stable and safe electrode array which is able to be inserted to a desired depth within the cochlea to provide useful percepts for the recipient which will not cause damage to the sensitive structures of the cochlea.

The present invention also aims to provide a device which can be used to provide electrical stimulation for high to medium frequency sounds and has the ability, should a deterioration in the ability to perceive medium to low sounds occur, to be easily adapted to apply electrical stimulation for a broad range of frequency sounds.

The present invention preferably provides a relatively very thin and short electrode array that is insertable into the basal region of the cochlea and past the first turn thereof. The electrode array preferably has minimal impact on the hydrodynamic behaviour of the cochlea and allows the user to gain maximum benefit from any residual hearing that they may possess.

According to a first aspect, the present invention is an implantable electrode array for insertion or which is insertable into at least the basal region of the cochlea, the array comprising:
   an elongate carrier having a proximal end, a distal end, and
      a plurality of electrodes supported by the carrier at respective spaced locations thereon in a region between the proximal end and the distal end; and
   a stabilising collar means extending outwardly from the elongate carrier at or adjacent a proximal end thereof, the stabilising collar means having an abutment surface adapted to abut at least a portion of the surface of the cochlea and at least substantially prevent movement of the carrier following completion of insertion of the array into the cochlea.

In one embodiment, the array can be insertable through a cochleostomy with the collar means adapted to abut at least a portion of the cochlea around the site of the cochleostomy.

In one embodiment of this aspect, the collar means can comprise a portion of the carrier having a diameter greater than that of the remainder of the carrier. The diameter of the collar means can be constant along its length. In another embodiment, the diameter of the collar means can vary along its length.

In one embodiment, the collar means can have a first portion in which the diameter of the collar means expands away from the proximal end of the collar means. In this embodiment, the diameter can expand frusto-conically. The frusto-conical portion can comprise between about 30% and 50% of the length of the collar means. The collar means can further comprise a second portion distal the proximal end of the collar means. The second portion is preferably constant in diameter along its length. The second portion preferably comprises between about 70% and 50% of the length of the collar means.

In one embodiment, the distal end of the collar means provides or comprises the abutment surface. The abutment surface preferably extends outwardly from the carrier for a length. In a further embodiment, the abutment surface extends outwardly substantially at a right angle, more preferably at a right angle, to the longitudinal axis of the carrier, when the carrier is straight. As such, the abutment preferably provides a corner in the outer surface of the carrier that is adapted to abut the surface of the cochlea in the region around the site of insertion once the array has been inserted into place within the cochlea. This abutment preferably at least substantially prevents subsequent lateral movement of the array relative to the cochlea.

The collar means is preferably positioned at the proximal end of the carrier. In a further embodiment, the collar means can be formed integrally with the carrier member. For example, the collar means can be moulded about the carrier member. In another embodiment, the collar means can be fabricated separately and connected to the carrier member.

In another embodiment, the stabilising collar is made of a flexible material at least similar to that used to form the carrier. Where the carrier is fabricated from a silicone compound, the stabilising collar means is also preferably fabricated from a silicone compound, including the same silicone compound or a different silicone compound.

In a further embodiment, the array can further comprise an anchoring means extending outwardly from the collar means. The anchoring means is preferably adapted to be attached or anchored with body tissues and/or bone at or proximate the cochleostomy site. In one embodiment the anchoring means preferably extends outwardly at or adjacent the abutment surface of the collar means. In one embodiment, the anchoring means can be made of a mesh material, such as Dacron. Sutures can preferably be passed through the mesh material and into the tissue and/or bone to secure the mesh to the tissue and/or bone. In one embodiment, the anchoring means is adapted to be sutured to the promontory bone.

In one embodiment, the mesh material comprising the anchoring means is moulded at least partially within the collar means. The mesh is preferably moulded at or adjacent the distal end of the collar means. The mesh preferably extends for a diameter that is at least about twice the diameter of the collar means. Other diameters of the mesh can be envisaged.

In one embodiment of this aspect, the array is preferably insertable within a cochlea to a depth that is at or beyond the first basal turn of the cochlea. In one embodiment, the array is insertable just beyond the first basal turn of the cochlea.

According to a second aspect, the present invention is an implantable electrode array for insertion into at least the basal region of the cochlea, the array comprising:
   an elongate carrier having a proximal end, a distal end, and
      a plurality of electrodes supported by the carrier at respective spaced locations thereon in a region between the proximal end and the distal end; and
   an anchoring means extending outwardly from the elongate carrier at or adjacent a proximal end thereof and adapted to be anchored to body tissues or bone surrounding the site of insertion and at least substantially prevent movement of the carrier following completion of insertion of the array into the cochlea.

In one embodiment of this aspect, the array can be insertable through a cochleostomy.

In this aspect, the anchoring means can be made of a mesh material, such as Dacron. Sutures can preferably be passed through the mesh material and into the tissue and/or bone to secure the mesh to the tissue and/or bone. In one embodiment of this aspect, the anchoring means is adapted to be sutured to the promontory bone.

In a further embodiment of this aspect, the mesh material comprising the anchoring means is moulded into place within the body of the carrier. The mesh is preferably moulded at or adjacent a proximal end of the carrier. The mesh preferably extends for a diameter that is at least about three times the diameter of the carrier. Other diameters of the mesh can be envisaged.

In one embodiment of this aspect, the array is preferably insertable within a cochlea to a depth that is at or beyond the first basal turn of the cochlea. In one embodiment, the array is insertable just beyond the first basal turn of the cochlea.

In one embodiment of both of the above aspects, the carrier can adopt a first configuration selected to allow the array to be inserted into a recipient's cochlea and at least a second configuration wherein said electrode array is adapted to apply tissue stimulation. The carrier is preferably formed to preferentially adopt the second configuration or another configuration different to said first configuration. The first configuration of the carrier can be substantially straight or exactly straight. In another embodiment, the first configuration can have a degree of curvature. In this embodiment, a distal portion of the carrier can have a degree of curvature. In this case, the distal portion can comprise less than about 20% of the length of the carrier.

In a further embodiment of both aspects, the elongate carrier preferably has a length of between 8-12 mm. As described, the length can be such that the carrier is insertable to a depth that just extends beyond the first turn of the cochlea from the cochleostomy.

In a still further embodiment of both aspects, at least one of the electrodes has a surface that is at least adjacent an inner surface of the carrier. More preferably, each of the electrodes in the array have a surface that is adjacent the inner surface of the carrier. In a further embodiment, the surfaces of the electrodes are aligned with the inner surface of the carrier. In another embodiment, the surfaces of the electrodes stand proud of the inner surface of the carrier. It is also envisaged that the electrode surface could also be recessed into the inner surface of the carrier. In yet another embodiment, one or more electrodes may also be positioned on the outer surface of the carrier not facing the modiolus. Such electrodes could act as additional ground or reference electrodes.

In yet another embodiment of both aspects, an indicator means may also be incorporated in the collar of the elongate carrier or at another location on the carrier to convey to the surgeon the orientation of the electrodes on the array. It is envisaged that the indicator means could be any means capable of representing an orientation of the array whereby the electrodes can be positioned as desired within the cochlea. In order to achieve this, the indicator means is preferably provided on the part of the array which is adapted to be positioned external to the cochlea following implantation of the carrier.

According to a third aspect, the present invention is a method of inserting an electrode array into at least the basal region of the scala tympani duct of a cochlea, said electrode array having a collar means attached thereto at or adjacent a proximal end thereof, the method comprising the steps of:
 (i) forming an opening into the cochlea to allow access to the scala tympani duct;
 (ii) inserting a distal end of said electrode array into the scala tympani duct and advancing the array therein; and
 (iii) at least abutting said collar means to the tissue surrounding said opening in the cochlea, wherein said collar at least partially seals said opening into the cochlea and is arranged so that the electrode array is stabilised within the cochlea.

In this aspect, the electrode array and collar means can have the features of the array and collar means as defined herein.

In a further embodiment of this aspect, the method can comprise an additional step prior to step (ii), in which a facia washer is fabricated and placed over said electrode array prior to its insertion into the cochlea. The facia washer can comprise a piece of temporalis fascia that is harvested from the recipient. The facia washer can have dimensions of 3 mm×3 mm. Once harvested, the washer can be pressed in a fascia press, before a sharp round instrument, such as a straight pick, is used to create a hole (eg. 0.4 mm in size) in the central portion of the stamp-like piece of fascia. The tip of the electrode is then passed through the hole until the fascia abuts the dacron mesh. The electrode is then placed into the cochleostomy. The fascia washer assists in sealing the inner ear from the middle ear.

In this aspect, the array can further comprise an anchoring means extending outwardly from the collar means and wherein the method comprises an additional step of attaching said anchoring means to the tissue and/or bone at or proximate the site of insertion. In one embodiment, the anchoring means can be sutured to the tissue and/or bone.

According to a fourth aspect, the present invention is a method of inserting a cochlear electrode array into at least the basal end of the scala tympani duct of a cochlea, said cochlear electrode array having an anchoring means extending outwardly therefrom at or adjacent a proximal end thereof, the method comprising the steps of:
 (i) forming an opening into the cochlea to allow access thereto;
 (ii) inserting a distal end of said electrode array into the scala tympani duct and advancing the array therein; and
 (iii) suturing said anchoring means to the tissue and/or bone surrounding said opening in the cochlea so as to stabilise the array within the cochlea.

In this aspect, electrode array and anchoring means can have the features of the array and anchoring means as defined herein.

In both the third and fourth aspects, the step of forming an opening to the cochlea can be performed via a normal cochleostomy using either a "soft surgery" technique with a diamond drill or laser to create a (eg. 0.5 mm) cochleostomy anterior and caudal to the round window.

In the third and fourth aspects, the electrode array is preferably formed with at least some degree of curvature and can be inserted into the cochlea in a straight configuration, using a straightening stylet or with a degree of curvature less than it normally adopts in a relaxed condition. Following insertion to a depth of preferably about 10-12 mm, the straightening stylet is preferably removed and the array is allowed to return to its relaxed curved configuration. In this embodiment, a distal portion of the carrier can have a degree of curvature when the carrier is in its relaxed condition. In this case, the distal portion can comprise less than about 20% of the length of the carrier.

Following insertion, the electrode array would be positioned in a manner whereby the electrodes are able to apply stimulation to the appropriate regions of the cochlea that detect sounds having high frequencies. The remaining structure of the cochlea would remain intact and allow the recipient to continue to use their residual hearing capability to detect sounds associated with middle to low frequency ranges.

In a further aspect, the present invention is an implantable component of a cochlear implant system, the implantable component comprising:
 a housing for a stimulator unit, the stimulator unit being adapted to output one or more stimulation signals;
 a first elongate electrode assembly selectively activatable to apply electrical stimulation in accordance with the output of the stimulator unit; and
 a second elongate electrode assembly selectively activatable to apply electrical stimulation in accordance with the output of the stimulator unit;
 wherein only one of said first and second electrode assemblies is insertable into the cochlea at any particular time.

In this aspect, the first elongate electrode assembly preferably has less electrodes than said second electrode assembly and is adapted, when inserted in the cochlea, to apply stimulation to the basilar region of the scala tympani of the cochlea. In one embodiment, the first electrode assembly can have six electrodes. In another embodiment of this aspect, the first electrode assembly can comprise the implantable electrode array according to the first or second aspects of the present invention.

In this aspect, the second electrode assembly is adapted, when inserted in the cochlea, to apply stimulation to the basilar region of the scala tympani and also to the region beyond the first basal turn. In one embodiment, the second electrode assembly can comprise an electrode assembly having 22 or 30 electrodes as is known in the art.

In this aspect, while the first electrode assembly is inserted in the cochlea, the second electrode assembly is preferably positioned external to the cochlea and is inoperative. While the second electrode assembly is inoperative, it is preferably coiled in the mastoid or is stored in a biocompatible package, such as a Teflon sack. While the second electrode assembly is inserted in the cochlea, the first electrode assembly is preferably positioned external to the cochlea and is inoperative.

The second electrode assembly may never be required but is implanted and is ready, in a subsequent surgery, to be inserted into the cochlea and rendered operable, if the recipient's hearing has deteriorated to the extent that they also no longer, at least readily, perceive middle to low frequencies.

According to yet another aspect, the present invention is a method of operating a cochlear implant system, said system comprising:
 a housing for a stimulator unit, the stimulator unit being adapted to output one or more stimulation signals; and
 an elongate electrode assembly adapted to apply electrical stimulation to the cochlea of a recipient of the system in accordance with the output of the stimulator unit, the assembly having a proximal end and a distal end and comprising a plurality of electrodes disposed along its length between the proximal end and the distal end, one or more of the electrodes relatively closer to the proximal end being adapted to provide stimulation to the basilar region of the cochlea and one or more of the electrodes relatively closer to the distal end being adapted to provide stimulation to a location beyond the first basal turn of the cochlea;
 the method comprising the steps of:
  while ever the recipient is only unable to hear relatively high frequency sounds, only activating those one or more electrodes adapted to provide stimulation to the basilar region of the cochlea.

In this aspect, the elongate electrode assembly is preferably relatively thin so as to at least substantially maintain the hydrodynamic nature of the cochlea.

In this aspect, those electrodes relatively closer to the distal end of the assembly are preferably able to be selectively made activatable as the recipient's ability to perceive relatively lower frequencies deteriorates. In this regard, only six or some other number of electrodes may initially be operative and adapted to deliver stimulation to the basilar region of the cochlea. As the recipient's ability to perceive middle to low frequencies deteriorates, additional electrodes that are positioned more deeply into the cochlea can be activated and become capable of delivering electrical stimulation. For example, an additional three electrodes may be rendered capable of delivering stimulation, then a further three at a later time and so on until such time as all electrodes on the array are capable of delivering stimulation. It will be appreciated that an additional three electrodes is only provided as an example and that more or less additional electrodes may be rendered operative as required to meet the particular requirements of the recipient.

Activation of additional electrodes so as to render them capable of delivering electrical stimulation will preferably not require additional surgery. Rather, an external controller, as described below, will be used to modify the operation of the implantable component as required.

In all of the aspects, the electrode assembly preferably comprises a carrier member having a leading end that is insertable into a cochlea of a recipient and a trailing end distal the leading end. The elongate carrier member preferably has a plurality of electrodes mounted thereon. In one embodiment, the electrodes are mounted in a longitudinal array. Each of the electrodes have at least one wire, and possibly at least two, extending from each electrode back towards the trailing end of the carrier member.

The wires preferably extend back to the housing to at least a first feedthrough in the wall of the housing of the stimulator unit. In one embodiment, the feedthrough provides hermetic and insulated electrical connection for each wire extending from the electrode assembly into the housing of the implantable component. Each feedthrough can be formed using the method described in U.S. Pat. No. 5,046,242, the contents of which are incorporated herein by reference. The electrodes are preferably formed from a biocompatible electrically conducting material, such as a suitable metal, such as platinum.

The elongate carrier member is preferably formed from a resiliently flexible material. In one embodiment, the carrier member can be preformed from a plastics material with memory.

In a preferred embodiment, the elongate carrier member is formed from a suitable biocompatible material. In one embodiment, the biocompatible material can be a silicone, such as a flexible silicone elastomer-Silastic. Silastic MDX 4-4210 is an example of one suitable silicone for use in the formation of the elongate member. In another embodiment, the elongate carrier member can be formed from a polyurethane or similar material.

In a preferred embodiment of the aspects, the implantable component can further comprise an additional electrode assembly that is adapted to be implantable external of the internal passages of the cochlea. This additional extracochlear electrode assembly is typically implanted external of the cochlea in the muscle surrounding the head of the user.

The use of this additional assembly allows the stimulation method known as monopolar stimulation to be performed. In monopolar stimulation, the stimulation passes between an intracochlear and an extracochlear electrode, providing for a relatively wide current spread.

In a further embodiment, the housing for the stimulator used in conjunction with the electrode array is preferably implantable in a recess of the temporal bone adjacent the ear of the recipient that is receiving the output of the implant system. The housing is preferably formed from a biocompatible material or has a biocompatible coating. The housing can be coated with a layer of silicone or parylene.

The system preferably relies upon a receiver antenna to receive radio frequency (RF) signals. The receiver antenna preferably comprises a wire antenna coil. The antenna coil can be comprised of at least one, and preferably at least three, turns of electrically insulated platinum or gold wire tuned to parallel resonance by a capacitor internal to the housing. The electrical insulation of the receiver antenna can be provided by a thin, flexible silicone moulding and/or silicone or polyurethane tubing.

The receiver antenna is preferably external of the housing of the stimulator unit. The moulding of the receiver antenna can also extend around at least some of the housing of the stimulator unit. Electrical connection between the antenna and componentry of the implantable componentry within the housing can be provided by two hermetic and electrically insulated ceramic feedthroughs or an electrical conductor. The ceramic feedthroughs can be formed using the method described in abovementioned U.S. Pat. No. 5,046,242.

The receiver antenna of the implantable component preferably acts as part of a radio frequency (RF) link to allow transcutaneous bidirectional data transfer between the implantable component and an external component of the system. The link preferably further comprises an external antenna that is able to be aligned with the position of the implantable receiver antenna. The radio frequency signals can be modified to encode data using the method described in U.S. Pat. No. 5,741,314. While described as a receiver antenna, the receiver antenna can preferably also transmit signals back to the transmitter antenna which receives the signals for the purpose of telemetry from the implanted component.

The link between the two antennae also provides a means of powering the componentry of the internal component. In the case where the implantable component further has an on-board or implantable power source, such as a rechargeable battery, the link can provide a means of inductively charging the battery when required.

When implanted, the housing preferably contains, in addition to the stimulator unit, a receiver unit. The receiver unit is preferably adapted to receive signals from an external component that comprises at least a controller. The controller is, in use, preferably mounted external to the body of the recipient such that the signals are transmitted transcutaneously through the skin of the recipient.

The external controller can have a housing for a speech processor adapted to receive signals output by a microphone. During use, the microphone can be mounted in the housing that is preferably supported on the pinna of the recipient. Other suitable locations for the microphone and/or the housing can be envisaged, such as a lapel of the recipient's clothing.

The speech processor encodes the sound detected by the microphone into a sequence of electrical stimuli following given algorithms, such as algorithms already developed for cochlear implant systems. The encoded sequence is transferred to the implanted receiver/stimulator unit using the transmitter and receiver antennae. The implanted receiver/stimulator unit demodulates the modulated signal and allocates the electrical pulses to the appropriate attached electrode by an algorithm which is consistent with the chosen speech coding strategy. Allocation is also consistent with the number of electrodes present in the array and/or the number of electrodes of the array that are in fact operative at that time.

The external controller preferably further comprises a power supply. The power supply can comprise one or more rechargeable batteries. The transmitter and receiver antennae are used to provide power via transcutaneous induction to the implanted receiver/stimulator unit and the electrode array.

In a further embodiment, the receiver coil can be disposed about a magnet. The magnet, when present, is preferably centrally disposed in the receiver coil. When present, the magnet can be used to hold and align an external coil mounted to the outside of the head of the recipient. To achieve, this a ferromagnetic material or another magnet arranged to experience an attraction force to the magnet within the receiver coil can be positioned in a central location within the external coil.

In one embodiment, the magnet can be removable from its location within the receiver coil.

While the implant system can rely on external componentry, in another embodiment, the controller, including the microphone, speech processor and power supply can also be implantable. In this embodiment, the controller can be contained within a hermetically sealed housing or the housing used for the stimulator unit.

BRIEF DESCRIPTION OF THE DRAWINGS

By way of example only, a preferred embodiment of the invention is now described with reference to the accompanying drawings, in which:

FIG. 2b is a medial side view of the electrode array of FIG. 2a;

PREFERRED MODE OF CARRYING OUT THE INVENTION

Figure 1:
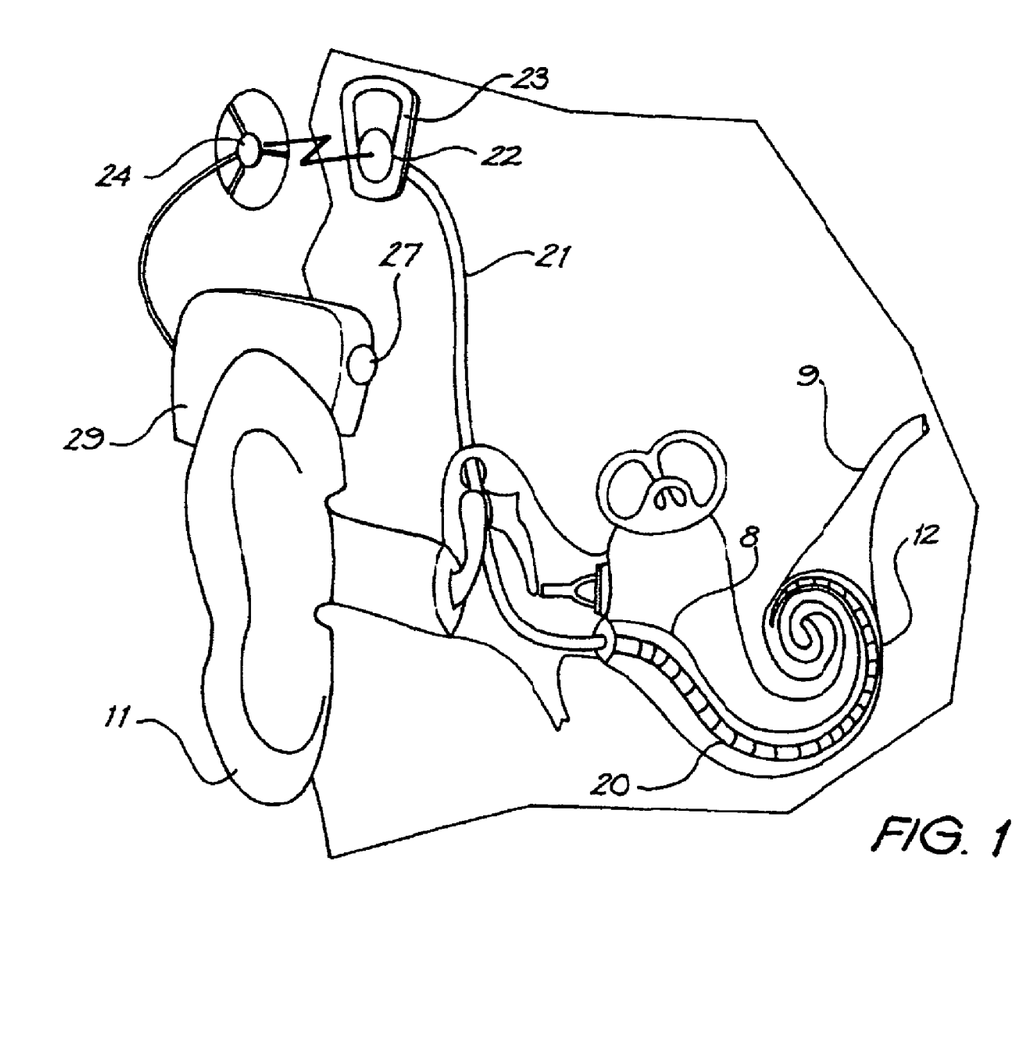
FIG. 1 is a pictorial representation of a prior art cochlear implant system.

Before describing the features of the present invention, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

Figure 2A:
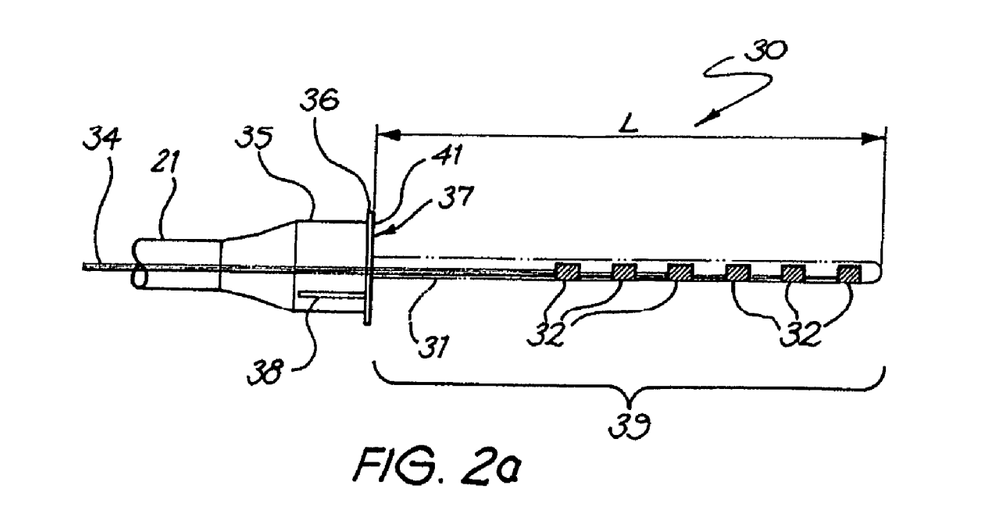
FIG. 2a is a side view of an electrode array made in accordance with the present invention.
Figure 2B:
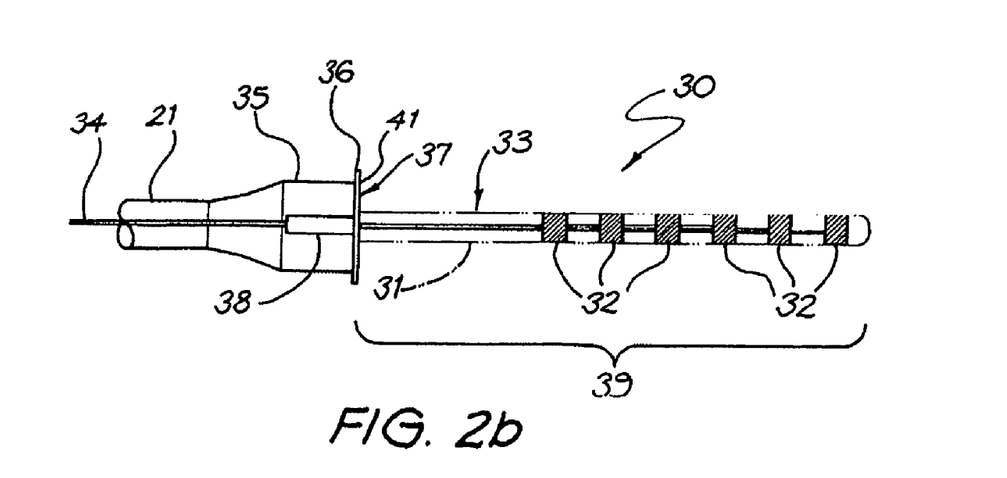

One embodiment of a cochlear implant electrode array, according to the present invention, is depicted generally as 30 in FIGS. 2a and 2b. FIG. 2a is the side view of the electrode array 30 and FIG. 2b is a view of the medial side of the electrode array 30. It can be considered that the medial side of the electrode array 30 is the side on which a plurality of spaced apart electrode contacts 32 are located.

As seen in FIGS. 2a and 2b, the electrode array 30 includes a plurality of spaced apart electrode contacts 32 on a flexible carrier 31. In a preferred embodiment, each of the electrode contacts 32 reside on the same side, the medial side 33, of the carrier 31. Each electrode contact 32 has at least one wire conductor 34 connected thereto. These wire conductors 34 are embedded within the flexible carrier 31 and exit through a proximal end of the carrier 31 within a flexible cable 21. As previously described the flexible cable 21, including the wire conductors 34, is connected to the implanted receiver and stimulator unit 22. The wires therefore provide the means for making electrical contact with each of the electrode contacts 32 from unit 22.

At the proximal end of the electrode array 30 is a collar 35. The collar 35 is larger in diameter than the carrier 31, and is made from a similar flexible material, such as silicone. The distal end of the collar 35 provides an abutment surface 37. Embedded within the collar 35 adjacent the surface 37 is an anchoring mesh material 36. In the depicted embodiment, the mesh material 36 is Dacron.

The right angle of the abutment surface 37 of the collar 35 with the outer surface of the carrier provides a square shoulder that at least substantially prevents the array 30 from twisting following insertion in the duct of a cochlea. The purpose of the mesh material 36 incorporated into and extending further outwardly that the collar 35 is to allow the face 41 of the mesh to be fixed and anchored to the promontory bone and integrated into the surrounding fibrous tissue. This collar 35 and anchoring mesh 36 combination overcomes the problems associated with movement of the short electrode over time, and prevents further penetration of the electrode array 30 into the cochlea, as well as aids greatly in sealing the cochleostomy.

The wire conductors 34 pass through the collar portion 35, exiting via the cable 21, which is connected to the collar portion 35 at its proximal end.

The electrode array 30 also includes an indicator means 38 incorporated into the collar 35 to assist the surgeon in determining the orientation of the electrodes 32, once inserted into the cochlea. As the portion of the array, shown generally as 39, is intended to be inserted into the cochlea with only the mesh material 36 and the collar 35 being external of the cochlear, it is important that the surgeon is provided with an indication as to the orientation of the surface of the array bearing the electrodes 32. In one embodiment, the indicator means could be a portion of Dacron mesh correctly positioned on the collar 35 via a fastening means such as glue, and covered with a clear silicone material, preferably the same material as that used to make the collar portion 35, to reform the tubular shape of the collar 35.

Alternatively, as opposed to the indicator means 38 being incorporated into the collar 35 as discussed above, the indicator means 38 can form part of the collar 35, such as include a silicone marking on the collar portion 35, or be in the form of a notch or other similar marking on the collar 35 or the mesh 36.

As shown in FIGS. 2a and 2b, the electrode contacts 32 are positioned on the medial side of the electrode array, i.e. positioned on the same side of the carrier 31. The array is preferably cylindrical and has a small diameter resulting in the volume of the array 30 being minimised. Preferably, the cross sectional area of the array is 0.2×0.4 mm. In normal hearing, the oscillation of the basilar membrane is required and the amplitude of the sound is dependant on the damping of the membrane motion by the fluid within the cochlea. Therefore, it is important that when an electrode array is inserted into the cochlea with the intention to preserve this natural capacity to detect sounds, as is the case with the present invention, the volume of the array must be minimised so that this damping will not be affected by the exclusion of the cochlea fluid. The electrode array 30 is of a smaller diameter than a conventional electrode array, and in the embodiment as shown, includes only 6 electrodes 32.

It is envisaged that whilst the overall shape of the electrode array is designed to be thin to reduce the volume of the electrode array, it is considered that the cross-section of the array could have a variety of shapes. In this regard, it is considered that the array could be round, oval, rounded square, hexagonal or octagonal and still fall within the spirit of the present invention.

Further, whilst the profile of the electrode array is shown as having a substantially constant diameter along its length of between 0.1 and 0.4 mm, it is also envisaged that the electrode array could have a tapered profile from 0.4 mm at its end joining the collar 35 to 0.1 mm at the tip, or any variation in between.

The length of the inserted portion of the array L is preferably set to be between 8-15 mm, more preferably between 9-12 mm. However it is envisaged that in one embodiment of the present invention, the electrode array could be as long as 20 mm as will be discussed in more detail below.

Figure 4:
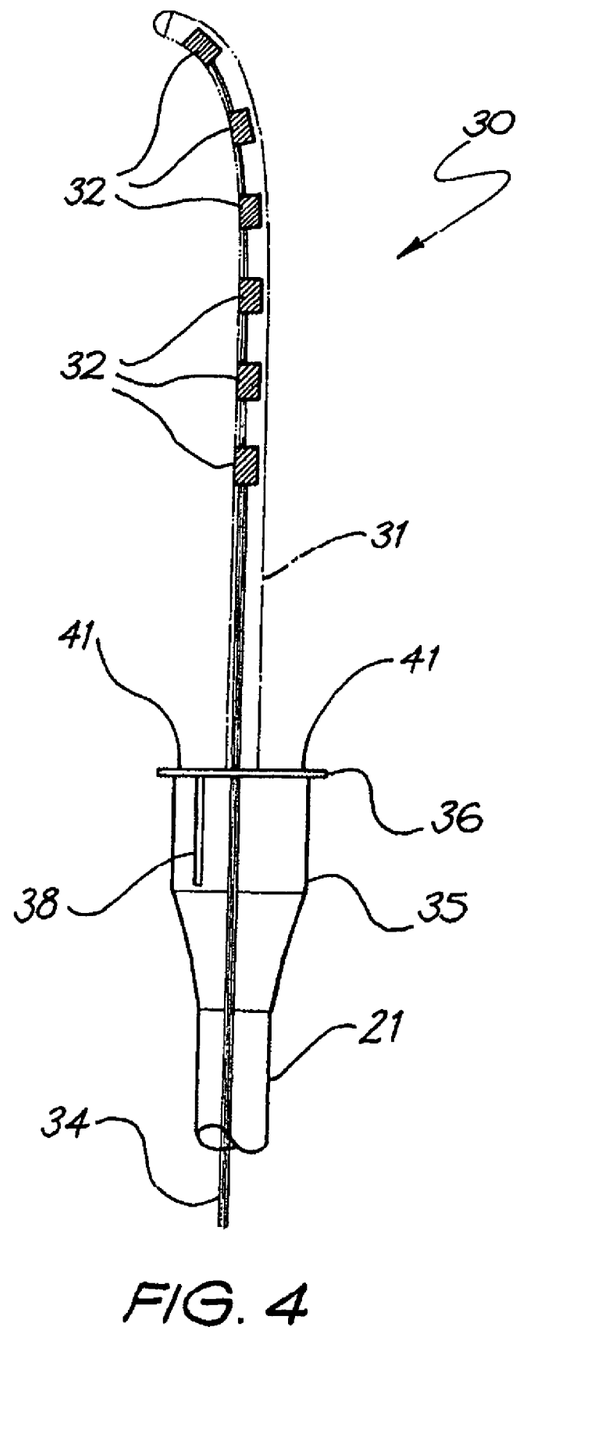
FIG. 4 is a view of an electrode of the present invention in its relaxed state.

In a preferred embodiment, the array 30 is constructed, such as by moulding, to have a slightly curved configuration when in its relaxed state, as is shown in FIG. 4. A stylet (not shown for clarity) can be used to hold the array in a straight (or at least substantially straight) configuration for insertion. The use of a straightening stylet is well known in the art and is discussed in detail in International Publication No WO 00/71063, the contents of which are incorporated herein by reference.

Figure 3:
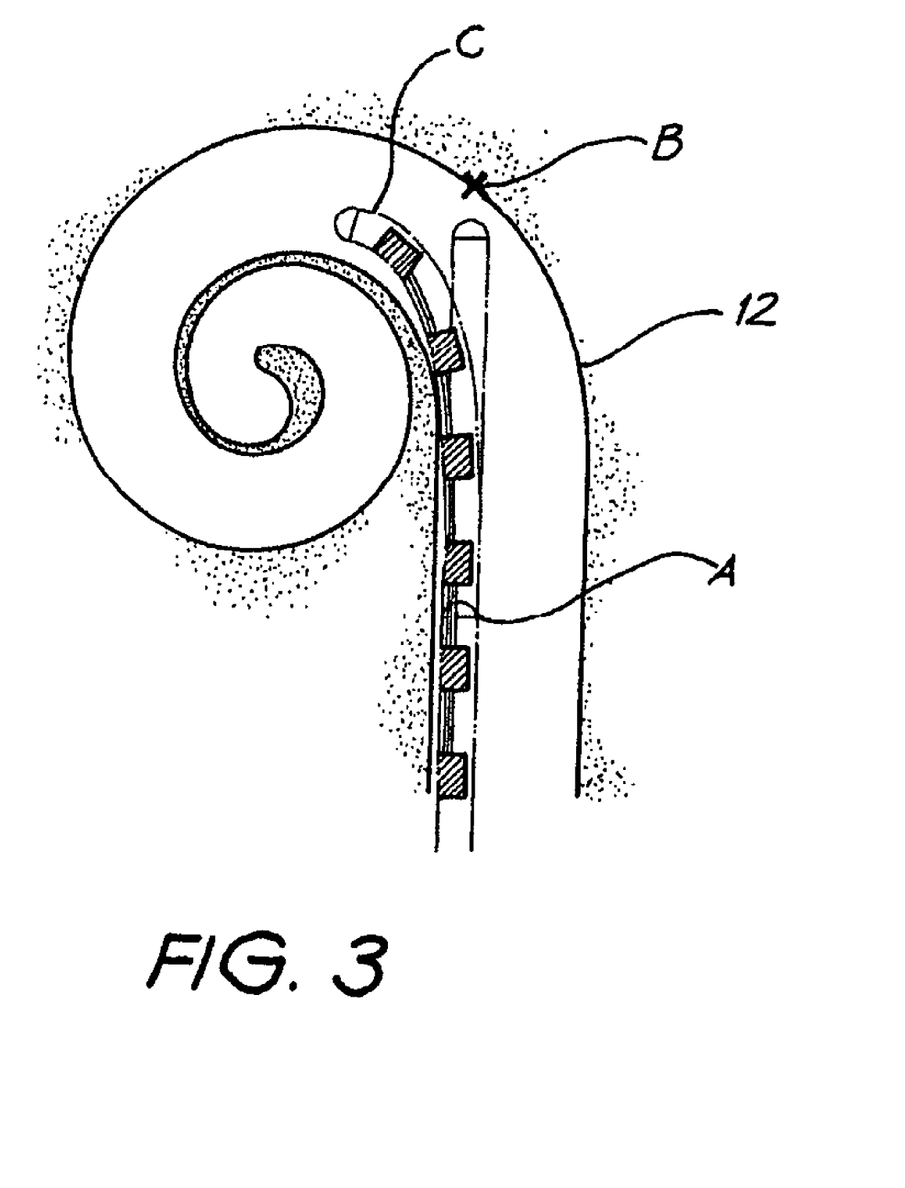
FIG. 3 is a simplified depiction of a cochlea representing issues associated with inserting shortened electrodes into the basal region of the cochlea.

FIG. 3 is a simplified view of a cochlea 12 showing issues associated with inserting short electrodes into the cochlea. It has been found experimentally that an electrode inserted to a depth that is between positions A & B will produce unnatural and sharp high pitch percepts for a recipient. In trials by the present applicant of a 6-electrode array inserted to a depth of 8 mm into the cochlea, it was found that recipients could not fuse the electrical stimulus with the auditory stimulus received. As a result, in such a device as described in International Publication No WO 00/69513, it is highly unlikely that such an electrode would provide benefit to the user. Therefore, in order to provide useful percepts to the recipient, the electrode array needs to be inserted beyond a depth of 6-8 mm. Providing this additional depth is, however, a challenge without damaging the osseous spinal lamina and basilar membrane.

As described previously, for devices such as the present invention, it is essential that the hydrodynamic nature of the cochlea be preserved in order to preserve the recipient's residual hearing. In order to achieve this it is essential that the sensitive structures of the cochlea be maintained and that the array does not damage the walls of the cochlea to alter the motion of the cochlea fluid. If the array is to be inserted beyond position A depicted in FIG. 3, and to the desired depth to provide useful benefit to the recipient, the array must be prevented from contacting the rear wall of the cochlea, shown as position B in FIG. 3. Therefore, in order to achieve this additional depth without causing damage to the structure of the cochlea, the array is shaped with at least some degree of curvature to extend past the first turn of the cochlea, as shown as C in FIG. 3.

FIG. 4 shows the device of the present invention that is capable of achieving the required depth of insertion. As shown, the array 30 is of a curved configuration with each of the electrode contacts 32 positioned on the same side of the carrier for stimulation of the desired regions of the cochlea. The array can be inserted into the cochlea in a straight configuration with the use of a straightening stylet (not shown) inserted into a lumen in the carrier 31. Upon insertion, the stylet can be removed allowing the array 30 to assume its natural pre-curved shape. In this regard, the electrode array is able to settle close to the modiolus under the osseous spinal lamina to minimise impact on the hydrodynamic nature of the cochlea. It is envisaged that the array could also have the electrode contacts 32 positioned on diametrically opposed surfaces of the carrier 31, rather than on the same surface and still fall within the scope of the present invention. It is also envisaged that instead of a straightening stylet being used to maintain the array in a straight position, a bioresorbable stiffening sheath could also be employed to maintain the array in a straight position, with the sheath being dissolvable upon contact with cochlear fluid or saline solution allowing the array to return to its pre-curved position.

Figure 5:
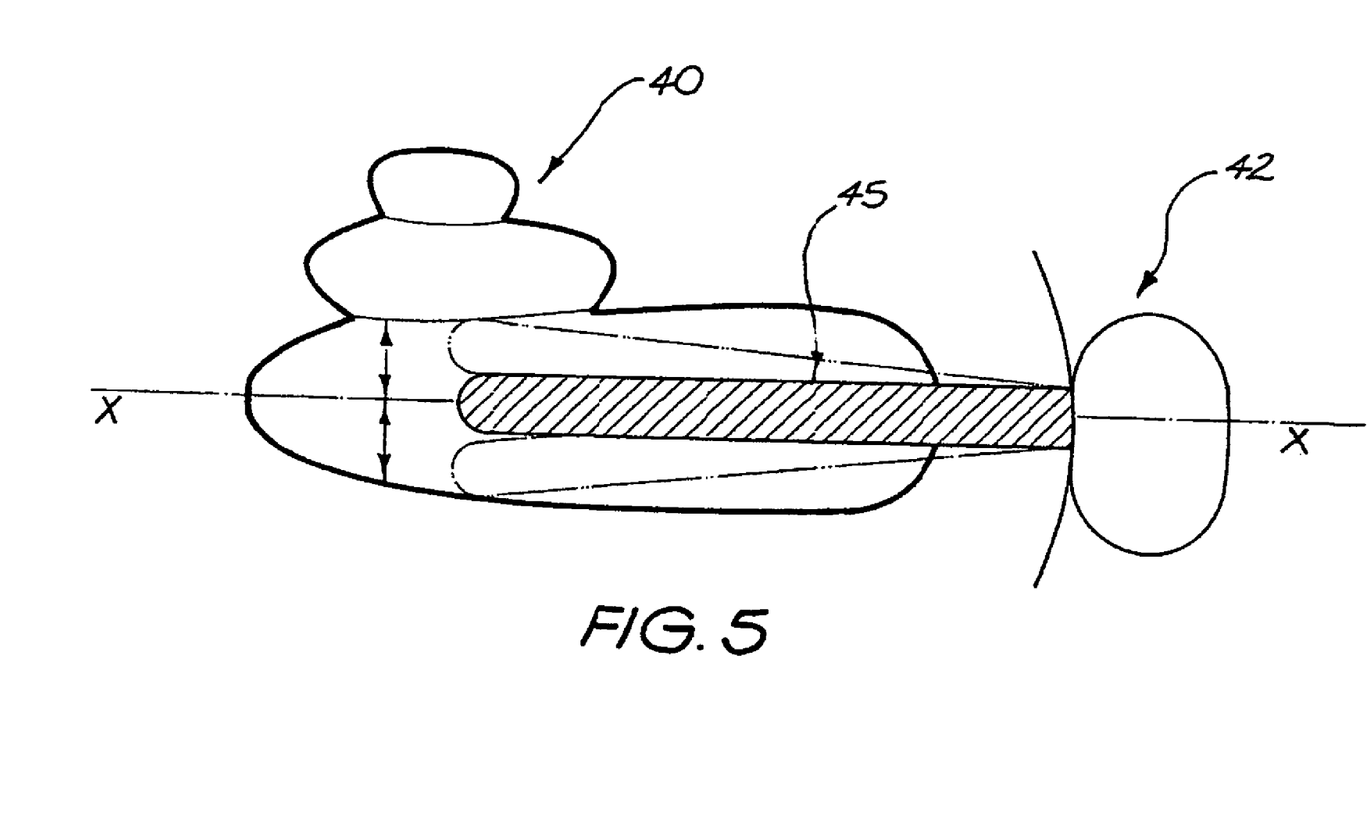
FIG. 5 is a further simplified depiction of a cochlea representing further issues associated with inserting shortened electrodes into the basal region of the cochlea.

FIG. 5 shows a further problem associated with prior art devices postulated to perform the task of the present invention. One of the major problems with prior art devices intended for insertion into the basal section of the cochlea resides in the stability of the electrode. The fixation of the proximal end of the electrode is essential in providing the desired stability of the electrode and to ensure that the electrode will not move or twist and damage the basilar membrane and sensitive structures of the cochlea, thereby affecting the hydrodynamic nature of the cochlea. As is shown in FIG. 5, the cochlea is represented diagrammatically as reference numeral 40, with the prior art array being depicted as the shaded region shown by reference numeral 45. During natural body motion, unless the proximal end 42 of the electrode array is properly fixed, an electrode inserted this depth into the electrode will experience a certain degree of rotation or twisting about the axis X-X, causing the electrode to damage the basilar membrane and affect the ability of the cochlea to naturally detect sounds. This is particularly the case where the proximal end of the device is rounded or relies upon flexible flaps or the like to maintain the array in the desired position.

With regard to the electrode array of the present invention as shown in FIG. 2a, FIG. 2b and FIG. 4, the stability of the electrode is ensured through the design of the proximal end of the array. In this design the electrode array is provided with a collar 35 having an abutment surface 37 to stabilise the electrode and reduce any rotation of the device during natural body movement. Further to this, the collar 35 has a mesh portion 36 extending outwardly therefrom that allows the surgeon to anchor the collar to the promontory bone for integration into the fibrous tissue and additional stabilisation. It is considered that the action of this collar provides the desired stability to the device to enable the array to perform its desired function.

The electrode array of the present invention is preferably inserted into the cochlear in the following manner. As the intention of the present invention is to preserve as much of the recipient's residual hearing as possible so that only high frequency sounds are provided electrically, it is desirable that the structure of the cochlea is left intact as much as possible. Therefore, rather than incising the round window membrane, a cochleostomy is formed. The cochleostomy is preferably made 1 mm anteroinferior to the round window and is preferably achieved using either a "soft surgery" technique or by drilling with a diamond burr or laser. The electrode array is then inserted into at least the basal region of the cochlea and secured in place as mentioned above. Prior to closing the cochleostomy, tissue or muscle is packed behind the mesh to create a fascia washer. The fascia washer assists in sealing the cochleostomy and ensuring that the hydrodynamic nature of the cochlea is maintained.

The electrode array is preferably made using conventional techniques, from conventional materials, as is known in the cochlear electrode array art. One approach for making a cochlear electrode array according to the present invention is described in International Publication No WO 00/71063, the contents of which are incorporated herein by reference.

Figure 6:
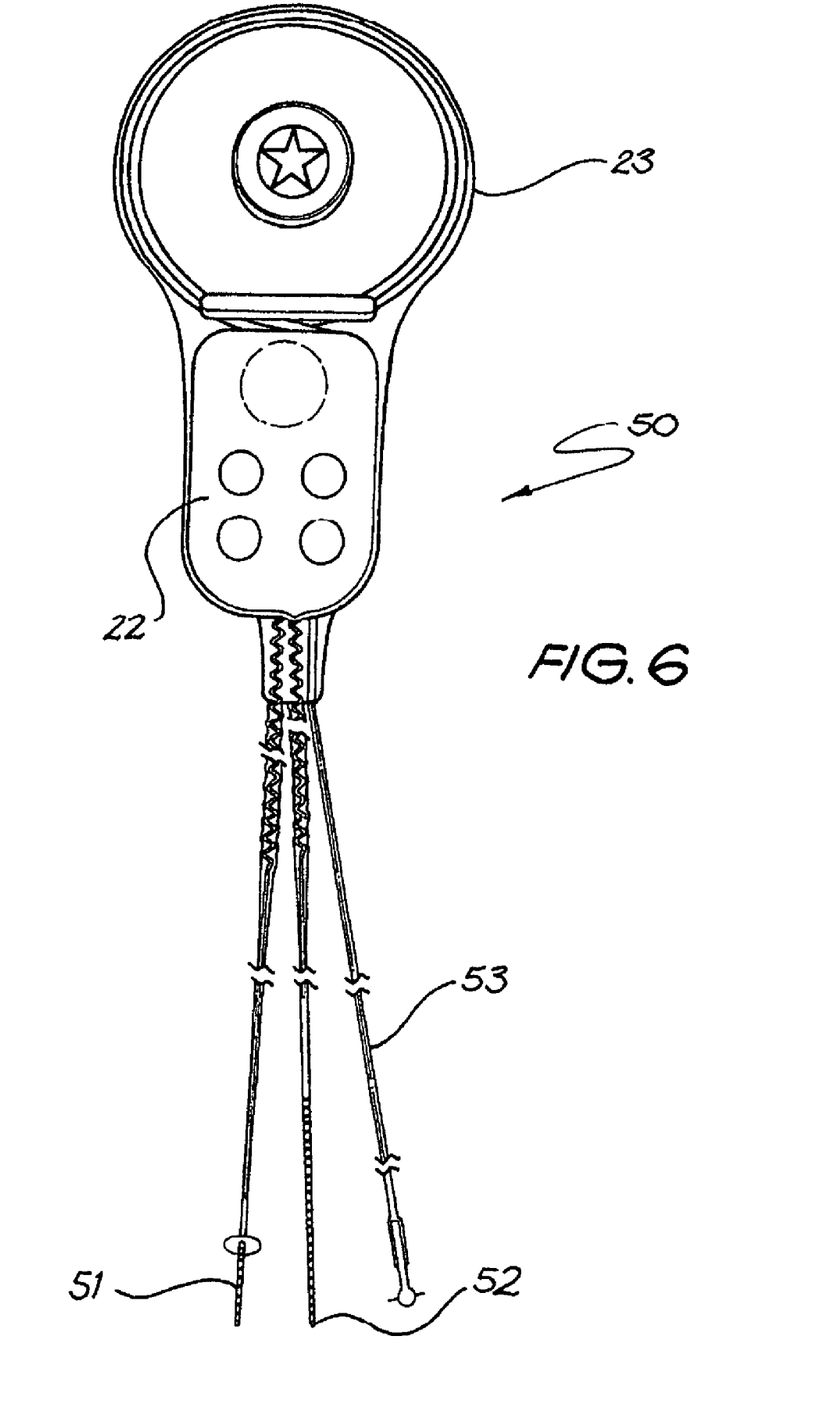
FIG. 6 shows an implantable device of a further embodiment of the present invention.

Turning to FIG. 6, there is shown the device of the present invention according to a further embodiment. In this embodiment, the device is shown generally as 50, and represents the implantable portion of the system. With reference to FIG. 1, the receiver coil 23 is shown as well as the receiver stimulator unit 22. Extending from the receiver stimulator unit 22 are three electrode arrays 51, 52, 53. Array 51 corresponds with the short electrode array having a collar as described above, which is inserted into the basilar region of the cochlear to provide electrical stimulation for high frequency sounds in accordance with the first embodiment of the present invention. Array 52 is essentially a conventional electrode array consisting of a plurality of electrodes arranged along the length thereof to provide electrical stimulation for sounds of all frequencies as is the case for conventional cochlear implant devices. Array 52 can be placed into the cochlea if further hearing loss occurs in the future. Array 53 is an extra cochlear electrode as is known in conventional cochlear implants which is positioned remote from the cochlear to provide a reference point for various modes of stimulation.

In this embodiment, a recipient can be implanted with the device 50 and the short array 51 can be inserted into the cochlea of the recipient to provide hearing sensation for sounds having a high frequency. In this case, the conventional array 52 can be stored for future use, either by coiling the array in the mastoid or packaged in a sack, made for example from Teflon, remote from the cochlea. In this regard, should the recipient perceive that middle to low frequency sounds are no longer being experienced through the residual hearing process, then the short array 51 could be simply removed and the conventional array inserted, thereby restoring sound perception for all sound frequencies in the same manner as a conventional cochlear implant device. In this embodiment, the device is easily upgraded to a conventional cochlear implant device should the need arise without the need for extensive explantation and revision surgery.

In yet another embodiment of the present invention, a thin electrode array of the same length as conventional electrode arrays could be inserted into the cochlea, having a plurality of electrodes positioned along the length thereof for applying stimulation to the surrounding regions of the cochlea. Such a thin array with reduced volume may be made by the technique as discussed in the Applicant's co-pending International Patent Application PCT/AU02/00272, the contents of which is incorporated herein by reference. In this construction, the implantable component may look quite similar to the component depicted in FIG. 6 but without electrode array 51. In this regard, the thin electrode array is fully inserted into the cochlea, however, only those most basal electrodes are "switched on" to apply stimulation to the cochlea representative of high frequency sounds. In this situation, the more apical electrodes are not active and the recipient relies upon the naturally present hair cells in the cochlea to receive and interpret the sounds. As the electrode array is of a small volume and a thin cross-section, natural hearing is possible and the hydrodynamic nature of the cochlea is preserved. In this embodiment, as the recipient's hearing deteriorates over time and the ability to perceive the middle to low frequency sounds deteriorates, the electrodes can be progressively activated to provide electrical stimulation over time, without the need to remove the electrode array from the cochlea.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for operating a cochlear implant comprising an elongate electrode assembly implanted in the cochlea having a first subset of electrodes implanted in the basilar region of the cochlea and a second subset of electrodes implanted beyond the first basal turn of the cochlea, the method comprising:
   activating the first subset of electrodes implanted in the basilar region; and
   applying stimulation to the basilar region with the first subset of electrodes while simultaneously allowing natural hearing to occur in one or more locations beyond the first basal turn in which the second subset of electrodes is implanted, wherein the electrodes of the second subset are inactive.

2. The method of claim 1, further comprising:
   activating at least one electrode of the second subset of electrodes and allowing natural hearing to occur in a first one of the one or more locations beyond the first basal turn.

3. The method of claim 2, wherein the second subset of electrodes comprises first and second groups of electrodes, and wherein activating at least one electrode of second subset of the electrodes comprises:
   activating the first group of electrodes and allowing natural hearing to occur in one or more locations beyond the first basal turn of the cochlea where the second group of electrodes is implanted.

4. The method of claim 2, wherein activating at least one electrode of the second subset of electrodes comprises:
   activating all of the electrodes of the second subset of electrodes.

5. The method of claim 4, further comprising:
   after activating all of the electrodes of the second subset, receiving sound comprising a first frequency component in a first frequency range and a second frequency component in a second frequency range;
   applying stimulation corresponding to the first frequency component to the basilar region with the first subset of the electrodes; and
   applying stimulation corresponding to the second frequency component to the one or more locations beyond the first basal turn with via the second subset of electrodes,
   wherein the basilar region corresponds to the first frequency range and the one or more locations beyond the first basal turn corresponds to the second frequency range.

6. The method of claim 2, further comprising:
   after activating the at least one electrode of the second subset, receiving sound comprising a first frequency component in a first frequency range and a second frequency component in a second frequency range; and
   applying stimulation corresponding to the first frequency component to the basilar region with the first subset of the electrodes and to a second one of the one or more locations beyond the first basal turn with the at least one electrode of the second subset, while allowing natural hearing of the second frequency component in the first one of the one or more locations beyond the first basal turn,
   wherein the basilar region and the second one of the one or more locations beyond the first basal turn correspond to the first frequency range and the first one of the one or more locations beyond the first basal turn corresponds to the second frequency range.

7. The method of claim 1, further comprising:
   receiving initial sound comprising a first frequency component in a first frequency range and a second frequency component in a second frequency range; and applying stimulation corresponding to the first frequency component of the initial sound to the basilar region with the first subset of electrodes while allowing natural hearing of the second frequency component of the initial sound in the one or more locations beyond the first basal turn,
   wherein the basilar region corresponds to the first frequency range and the one or more locations beyond the first basal turn corresponds to the second frequency range.

8. The method of claim 7, further comprising:
   after applying the stimulation corresponding to the first frequency component, activating at least one electrode of the second subset of the electrodes and allowing natural hearing to occur in a first one of the one or more locations beyond the first basal turn.

9. The method of claim 8, further comprising:
   after activating the at least one electrode of the second subset, receiving further sound comprising first and second frequency components; and
   applying stimulation corresponding to the first frequency component of the further sound to the basilar region with the first subset of electrodes and to a second one of the one or more locations beyond the first basal turn with the at least one electrode of the second subset, while allowing natural hearing of the second frequency component of the further sound in the first one of the one or more locations beyond the first basal turn.

10. The method of claim 9, further comprising:
    activating all of the electrodes of the second subset of electrodes after applying stimulation via the first subset of the electrodes and the at least one electrode of the second subset.

11. The method of claim 10, further comprising:
after activating all of the electrodes of the second subset, receiving additional sound comprising a first frequency component in the first frequency range and a second frequency component in the second frequency range;
applying stimulation corresponding to the first frequency component of the additional sound to the basilar region via the first subset of the electrodes; and
applying stimulation corresponding to the second frequency component of the additional sound to the one or more locations beyond the first basal turn of the cochlea via the second subset of electrodes,
wherein the basilar region corresponds to the first frequency range and the one or more locations beyond the first basal turn correspond to the second frequency range.

12. The method of claim 1, wherein the electrode assembly is dimensioned such that the hydrodynamic nature of the cochlea is substantially maintained after implantation of the electrode assembly in the cochlea.

13. The system of claim 12, wherein the electrode assembly has a sufficiently thin cross-section and a sufficiently small volume such that, when the electrode assembly is implanted, the electrode assembly does not prevent the recipient from hearing at least some frequencies using naturally present hair cells in the one or more locations beyond the first basal turn.

* * * * *